(12) United States Patent
Bolton et al.

(10) Patent No.: US 6,565,803 B1
(45) Date of Patent: May 20, 2003

(54) METHOD FOR THE INACTIVATION OF CRYPTOSPORIDIUM PARVUM USING ULTRAVIOLET LIGHT

(75) Inventors: James R. Bolton, Ontario (CA); R. D. Samuel Stevens, Moon Township, PA (US); Bertrand Dussert, Pittsburgh, PA (US)

(73) Assignee: Calgon Carbon Corporation, Pittsburgh, PA (US)

( * ) Notice: Subject to any disclaimer, the term of this patent is extended or adjusted under 35 U.S.C. 154(b) by 0 days.

(21) Appl. No.: 09/300,325

(22) Filed: Apr. 27, 1999

Related U.S. Application Data

(63) Continuation-in-part of application No. 09/078,116, filed on May 13, 1998, now Pat. No. 6,129,893.

(51) Int. Cl.[7] .................................................. C02F 1/32
(52) U.S. Cl. ............................ 422/24; 422/23; 210/748
(58) Field of Search ...................... 422/23, 24; 210/748

(56) References Cited

U.S. PATENT DOCUMENTS

| | | | |
|---|---|---|---|
| 2,072,416 A | 3/1937 | Berndt et al. | |
| 2,072,417 A | 3/1937 | Berndt et al. | |
| 2,438,168 A | 3/1948 | Hearst et al. | |
| 2,482,507 A | 9/1949 | Rentschler et al. | |
| 2,930,706 A | 3/1960 | Moulton et al. | |
| 3,462,597 A | 8/1969 | Young | |
| 3,814,680 A | 6/1974 | Wood | |
| 3,817,703 A | 6/1974 | Atwood | |
| 3,941,670 A | 3/1976 | Pratt | |
| 3,948,772 A | 4/1976 | Ellner | |
| 3,955,921 A | 5/1976 | Tensmeyer | |
| 4,042,325 A | 8/1977 | Tensmeyer | |
| 4,112,124 A | 9/1978 | Jarvis | |
| 4,141,686 A | 2/1979 | Lewis | |
| 4,179,616 A | 12/1979 | Coviello et al. | |
| 4,229,202 A | 10/1980 | Mullerheim et al. | |
| 4,230,571 A | 10/1980 | Dadd | |
| 4,265,747 A | 5/1981 | Copa et al. | |
| 4,296,066 A | 10/1981 | Schenck | |
| 4,304,996 A | 12/1981 | Blades | |
| 4,372,860 A | 2/1983 | Kaas | |
| 4,390,432 A | 6/1983 | Takeguchi | |
| 4,433,244 A | 2/1984 | Hogan | |
| 4,464,336 A | 8/1984 | Hiramoto | |
| 4,479,762 A | 10/1984 | Bilstad et al. | |
| 4,534,282 A | 8/1985 | Marinoza | |
| 4,535,247 A | 8/1985 | Kurtz | |
| 4,601,822 A | 7/1986 | Zamburro | |
| 4,623,467 A | 11/1986 | Hamlin | |
| 4,661,264 A | 4/1987 | Goudy, Jr. | |
| 4,766,321 A | 8/1988 | Lew et al. | |
| 4,769,131 A | 9/1988 | Noll et al. | |
| 4,816,145 A | 3/1989 | Goudy, Jr. | |
| 4,871,559 A | 10/1989 | Dunn et al. | |
| 4,902,411 A | 2/1990 | Lin | |
| 4,904,874 A | 2/1990 | Ellner | |
| 4,910,942 A | 3/1990 | Dunn et al. | |
| 4,952,511 A | 8/1990 | Radmer | |
| 4,968,891 A | 11/1990 | Jhawar et al. | |
| 4,971,687 A | 11/1990 | Anderson | |
| 5,034,235 A | 7/1991 | Dunn et al. | |
| 5,037,618 A | 8/1991 | Hager | |
| 5,118,422 A | 6/1992 | Cooper et al. | |
| 5,120,450 A | 6/1992 | Stanley, Jr. | |
| 5,124,131 A | 6/1992 | Wekhof | |
| 5,141,636 A | 8/1992 | Flanagan et al. | |
| 5,144,146 A | 9/1992 | Wekhof | |
| 5,151,252 A | 9/1992 | Mass | |
| 5,207,921 A | 5/1993 | Vincent | |
| 5,208,461 A | 5/1993 | Tipton | |
| 5,234,606 A | 8/1993 | Kazama et al. | |
| 5,235,905 A | 8/1993 | Bushnell et al. | |
| 5,256,299 A | 10/1993 | Wang et al. | |
| 5,364,645 A | 11/1994 | Lagunas-Solar et al. | |
| 5,389,254 A | 2/1995 | Sherman | |
| 5,433,866 A | 7/1995 | Hoppe et al. | |
| 5,441,179 A | 8/1995 | Marsh | |
| 5,443,733 A | 8/1995 | Mueller et al. | |
| 5,446,289 A | 8/1995 | Shodeen et al. | |
| 5,451,791 A | 9/1995 | Mark | |
| 5,466,425 A | 11/1995 | Adams | |
| 5,494,576 A | 2/1996 | Hoppe et al. | |
| 5,498,394 A | 3/1996 | Matschke | |
| 5,543,056 A | 8/1996 | Murcott et al. | |
| 5,545,335 A | 8/1996 | Sween et al. | |
| 5,582,741 A | 12/1996 | Kenmoku et al. | |
| 5,591,434 A | 1/1997 | Jenkins et al. | |
| 5,639,452 A | 6/1997 | Messier | |
| 5,675,153 A | * 10/1997 | Snowball ..................... 250/438 |
| 5,780,860 A | * 7/1998 | Gadgil et al. ............. 422/24 X |
| 5,785,845 A | 7/1998 | Colaiano | |
| 5,786,812 A | 7/1998 | Yoshikawa et al. | |
| 5,900,211 A | 5/1999 | Dunn et al. | |
| 5,935,431 A | 8/1999 | Korin | |
| 5,942,110 A | 8/1999 | Norris | |

FOREIGN PATENT DOCUMENTS

DE       1946267       1/1976

(List continued on next page.)

OTHER PUBLICATIONS

Furst, G. M.. Abstract of "Advanced ultraviolet irradiation of drinking water inactivates Cryptosporidium and other pathogens," Proc. Ann. Conf. of Americal Water Works Assoc., 1997.*

(List continued on next page.)

*Primary Examiner*—Elizabeth McKane
(74) *Attorney, Agent, or Firm*—Cohen & Grigsby, P.C.

(57) ABSTRACT

A method for the inactivation of Cryptosporidium oocysts, Giardia cysts and similar organisms comprising irradiating water with ultraviolet light in doses of from about 1 $mJ/cm^2$ to about 175 $mJ/cm^2$.

14 Claims, 2 Drawing Sheets

FOREIGN PATENT DOCUMENTS

| | | |
|---|---|---|
| DE | 2907887 | 9/1980 |
| EP | 0 003 879 | 2/1979 |
| EP | 0 005 235 | 4/1979 |
| EP | 0 027 278 | 10/1980 |
| EP | 0 270 879 | 11/1987 |
| EP | 0 317 735 | 9/1988 |
| EP | 0 316 687 | 11/1988 |
| EP | 0 343 998 | 5/1989 |
| EP | 0 634 362 | 7/1994 |
| EP | 0 643 016 | 9/1994 |
| EP | 0 671 363 | 9/1994 |
| EP | 0 686 601 | 5/1995 |
| EP | 0 721 920 | 1/1996 |
| EP | 0 806 398 | 4/1997 |
| EP | 0 968 962 | 6/1997 |
| GB | 364128 | 12/1931 |
| GB | 902760 | 2/1959 |
| GB | 1052513 | 12/1963 |
| GB | 1346521 | 2/1974 |
| GB | 1448411 | 9/1976 |
| GB | 1548997 | 7/1979 |
| GB | 1581998 | 12/1980 |
| GB | 2292097 | 2/1996 |
| GB | 2292097 A | 2/1996 |
| NL | 7502834 | 3/1975 |
| WO | WO 89/10069 | 11/1986 |
| WO | WO 88/03369 | 5/1988 |
| WO | WO 95/28095 | 10/1995 |
| WO | WO 96/25048 | 8/1996 |
| WO | WO 97/15332 | 5/1997 |
| WO | WO 98/05595 | 7/1997 |
| WO | WO 99/61375 | 3/1999 |
| WO | WO 99/52566 | 4/1999 |
| WO | WO 00/10923 | 7/1999 |
| WO | WO 00/10924 | 7/1999 |
| WO | WO 00/10925 | 7/1999 |

OTHER PUBLICATIONS

Clancy, J. et al. "UV light inactivation of Cryptosporidium oocysts," Journal of AWWA, vol. 90, No. 9, pp. 92–102, 1998.*

Water Supply, vol. 11, Amsterdam, pp. 103–118, 1993 entitled: "Effects of Disinfectants on the Viability of Cryptosporidium Parvum Oocysts" Authors: M.E. Ransome, T.N. Whitmore and E.G. Carrington.

"Inactivation of Oocysts of Cryptosporidium Parvum by Ultraviolet Irradiation" Wat. Res., vol. 29, No. 11, pp. 2583–2586 (1995) Authors: A.T. Campbell, L.J. Robertson, M.R. Snowball and H.V. Smith.

"Ultraviolet Sterilization" Handbook of Water Purification, second edition, Ellis Horwood Series in Water and Wastewater Technology, author: Gunther O. Schenk.

Jarol, E.L., "Effect of disinfectants on Giardia cysts," CRC Critical Reviews in Environmental Control, 1988, 18, 1–28.

M.J. Lorenzo–Lorenzo, M.E. Area–Mazea, I. Villacorta–Martinez de Maturana and Duran–Oreiro, "Effect of Ultraviolet Disinfection of Drinking Water on Viability of Cryptosporidium parvum Oocytes," J. Parasitol, 1993, 79(1), 67–70.

A. Bushnell, W. Clark, J. Dunn and K. Salisbury, "Pulsed Light Sterilization of Products Packaged by Blow–Fill–Seal Techniques," Pharm. Ngin. 1997, Set/Oct. 74–83.

A.T. Campbell, L.J. Robertson, M.R. Snowball and H.V. Smith, "Inactivation of Oocysts of Cryptosporidium parvum by Ultraviolet Irradiation" Wat. Res., vol. 29, No. 11, pp. 2583–2586 (1995).

Gunther O. Schenk, "Ultraviolet Sterilization" Handbook of Water Purification, second edition, Ellis Horwood Series in Water and Wastewater technology, prior art.

M.E. Ransome, T.N. Whitmore and E.G. Carrington, "Effects of Disinfectants on the Viability of Cryptosporidium parvum Oocysts" Water Supply, vol. 11, Amsterdam, pp. 103–118, 1993, XP002113177.

R. LaFrenz, "High Intensity Pulsed UV For Drinking Water Treatment" Proc. AWWA WQT Conference, Denver, CO, Nov. 1997.

Johnson, "Flashblast—the Light that Cleans", Popular Science, pp. 82–84, prior art.

Rentschler, et al., "Bactericidal Effect of Ultraviolet Radiation", Research Department, Westinghouse Lamp Division, Bloomfield, New Jersey, pp. 745–774, 1940.

Pulsed–Light Treatment of Food & Packaging, Dunn et al. Food Technology, vol. 49, No. 9, Sep. 1995, pp. 95–98.

Clancy, Hargy, Marshall, Dykson, "UV Light Inactivation of Cryptosporidium Oocysts," Waterborn Pathogens, vol. 90, Issue 9, Journal AWWA, 1998.

Furst, G. Michael, Jr., P.E., Product Manager, Safe Water Solutions LLC, "Advanced Ultraviolet irradiation of Drinking water Inactivates Cryptosporidium and Other Pathogens" American Water Works Association Proceedings, 1997 Annual Conference, Management & Regulations, vol. A (1 of 5) Jun. 15–19, 1997, Atlanta, Georgia.

Abbaszadegan M. et al, "The Disinfection Efficacy of a Point–of–Use Water Treatment System Against Bacterial, Viral and Protozoan Waterborne Pathogens" Water Research, NL, Elsevier Science Publishers, Amsterdam, vol. 31, No. 3, Mar. 1, 1997 (Mar. 1, 1997), pp. 574–582.

Rice E. W; Hoff J.C: "Inactivation of Giardia Lamblia by Ultraviolet Irradiation" Applied and Environmental Microbiology, vol. 42, No. 3, Sep. 1981 (1981–09), pp. 546–547 XP000949317.

Abstract: Pires, M.R., Pisani, B., Prandi, M.A.G., Simoes, M., "Desinfection of Water with Ultraviolet Radiation: Bactericide Efficiency" Journal–Revista do Instituto Adolfo Lutz, vol. 57, No. 1, 1998, pp. 29–34, Research Article, (NDN–0677–2758–3).

Abstract: Martinez, D., Farre, J., Borrull, F., Calull, M., Ruana, J., Colom, A., "Capillary Zone Electrophoresis With Indirect UV Detection of Haloacetic Acids in Water" Journal of Chromatography A, vol. 808, No. 1–2, 1998, pp. 229–236, Research Article, (NDN–007–0673–7062–0).

Parrotta, Bekdash, "UV Disinfection of Small Groundwater Supplies", Journal–American Water Works Association Journal, vol. 90, No. 2, 1998, pp. 71–81, ISSN 003–150X.

Abstract: Moreland, Rijal, G; Fujioka, R. V., "Evaluation of a UV System to Disinfect Wastewater From a 3 MGD Plant Based on Inactivation of Six Microbial Indicators", Journal–Abstracts o the General Meeting of the American Society for Microbiology, vol. 96, 1996, pp. 397, ISSN 1060–2011, Meeting Abstract, 96th General Meeting of the American Society for Microbiology, May 19–23, 1996, New Orleans, Louisiana (NDN–007–0552–6836–9).

Korshin, G., V.; Li, C–W; Benjamin, M.W., "A Theoretical Description of the UV Spectrum of Natural Organic Matter and Changes in UV Absorption During Water Treatment", Journal–Abstracts of Papers American Chemical Society, vol. 210, No. 1–2, 1995, pp. ENVR 133, Meeting Abstract, 210th American Chemical Society National Meeting, Aug. 20–24, 1995, Chicago, Illinois.

Kusnetsov, J.M.; Keskitalo, P.J.; Ahonene, H.E.; Tulkki, A.I.; Miettinen, I.T.; Martikainen, P.J., "Growth of Legionella and Other Heterotrophic Bacteria in a Circulating Cooling Water System Exposed to Ultraviolet Irradiation", Journal of Applied Bacteriology, vol. 77, No. 4, 1994, pp. 461–466, Research Article.

Rijal, G; Fujioka, R., "Evaluation of UV Disinfection System in the Inactivation of Various Indicator Organisms in Wastewater Effluents", Journal–Abstracts of the General Meeting of the American Society for Microbiology, vol. 94, 1994, pp. 388, Meeting Abstract, 94$^{th}$ General Meeting of the American Society for Microbiology, May 23, 27, 1994, Las Vegas, Nevada.

Abstract: Huber, S.; Popp, W., "Experiences with UV Irradiation of Purified Water for the Purpose of Germ Reduction," Meeting Paper, Biological Abstracts/RRM vol. 046, Iss. 006, Ref. 082899, German, pp. 290–305, (NDN–007–0440–6348–2), prior art.

Kolch, Andreas, "Disinfecting Drinking Water with UV Light", Journal–Pollution Engineering, vol. 31, No. 10, pp. 34–36, Oct. 1999.

Abstract: Miyamoto, M; Yamaguchi, Y.; Sasatsu, M., "Disinfectant Effects of Hot Water, Ultraviolet Light, Silver Ions and Chlorine on Strains of Legionella and Nontuberculous Mycobacteria," Journal–Microbios, vol. 101, No. 398, pp. 7–13 (NDN–122–0207–2336–1), prior art.

Hancock, George, G.; Davis, Ernst M., "Regrowth Potential of Coliforms after UV Disinfection of Municipal Wastewater," Journal–J Envir Sci Health Pt A, vol. 34, No. 9, pp. 1737–1743, Journal Article, 1999.

Loge, et al., Factors Influencing Ultraviolet Disinfection Performance Part I: Light Penetration to Wastewater Particles, Journal–Water Environment Research Ywater Environ Res, vol. 71, No. 3, pp. 377–381, Jun. 1999.

Loge, et al., Factors Influencing Ultraviolet Disinfection Performance Part II: Light Penetration to Wastewater Particles, Journal–Water Environment Research Water Environ Res, vol. 71, No. 6, pp. 1178–1187, Oct. 1999.

Abstract: Diaz, M.E.; Law, S.E., "Ultraviolet Photon Enhanced Ozonation for Microbiological Safety in Poultry Processing Water," Book Monograph, PAP ASAE, vol. 3, 13 pp., Meeting Reports, 1997 (NDN–122–0185–1573–2).

Baron, J.; Bourbigot, M.M., "Repair of *Escherichia coli* and Enterococci in Sea Water After Ultraviolet Disinfection Quantification Using Diffusion Chambers", Journal–Water Res., vol. 30, No. 11, pp. 2817–2821, 1996.

Sommer, R.; Cabaj, A., "Evaluation of the Efficiency of a UV Plant for Drinking Water Disinfection," Journal–Water Sci. Technol., vol. 27, No. 3–4, pp. 357–362, 1993.

Sobotka, J., "The Efficiency of Water Treatment and Disinfection by Means of Ultraviolet Radiation," Journal–Water Sci. Technol., vol. 27, No. 3–4, pp. 343–346, 1993.

Wiedenmann, A. Fischeter, B; Straub, U.; Wang, C.-H.; Flehmig, B; Schoenen, D., "Disinfection of Hepatitis A Virus and MS-2 Coliphage in Water by Ultraviolet Irradiation: Comparison of UV–Susceptibility," Journal–Water Sci. Technol., vol. 27, No. 3–4, p. 335–338, 1993.

Whitby, G.E.; Palmateer, G., "Effect of UV Transmission, Suspended Solids and Photoreactivation on Microorganisms in Wastewater Treated with UV Light," Journal–Water Sci Technol, vol. 27, No. 34– pp. 379–386, 1993.

Hengesbach, B.; Schoenen, D.; Hoyen, O; Bernhardt, H.; Mark, G.; Schuchmann, H.P.; von Sonntag, C., "UV Disinfection of Drinking Water—The Question of Bacterial Regrowth and the Photolytic Degradation of Biogenic High–Molecular–Weight Substances," Journal–Aqua, vol. 42, No. 1, pp. 13–22, 1993.

Abstract: Kolman, R., "Use of UV Radiation for Disinfecting Water in First Stage Growth Tanks Stocked with Rainbow Trout (Oncorhynchus Mykiss) Larvae," Journal–Rocz. Nauk Noln. Ser. H Rybactwo, vol. 102, No. 1, pp. 71–86, 1989 (NDN–122–0118–6891–1).

Abstract: Grigor'eva, L. V.; Korchak, G.I.; Bei, T. V., "Stability and Reactivation in Water of Adhesiveness and Coliciogenicity of Enterobacteria Under Action of Ultraviolet Radiation," Journal–Khim Tekhnol Vody, Vo. 14, No. 10, pp. 794–799, 1992 (NDN–122–0117–8831–7).

Sobotka, M, et al., "Application for Ultraviolet Radiation for Water Disinfection and Purification in Poland," Journal–Water Sci. Technol., vol. 26, No. 1–12, pp. 2313–2316, 1992.

Sundstrom, D. W.; Weir, B.A.; Barber, T.A.; Klei, H.E.; "Destruction of Pollutants and Microorganisms in Water by UV Light and Hydrogen Peroxide," Journal–Water Pollut Res J Can, vol. 27, No. 1, pp. 57–68, 1992.

Caufield, J.D., "Specifying and Monitoring Ultraviolet Systems for Effective Disinfection of Water," Journal–AM Fish. Soc. Symp., No. 10, pp. 421–426, 1991.

Nieuwstad, T.J.; Havelaar, A.H.; Van Olphen, M., "Hydraulic and Microbiological Characterization of Reactors for Ultraviolet Disinfection of Secondary Wastewater Effluent," Journal–Water Res., vol. 25, No. 7, pp. 775–783, 1991.

Havelaar, A.H.; Nieuwstad, T.J.; Meulemans, C.C.E.; Van Olphen, M., "F–Specific RNA Bacteriophages as Model Viruses in UV Disinfection of Wastewater," Journal–Water Sci. Technol., vol. 24, No. 2, pp. 347–352, 1991.

Zemke, V.; Podgorsek, L.; Schoenen, D., Ultraviolet Disinfection of Drinking Water. 1. Communication: Inactivation of *E. coli* and Coliform Bacteria, Journal–Zentralbl. Hyg. Mweltmed., vol. 190, No. 1–2, pp. 51–61, 1990.

Oliver–Daumen, B.; Bach, W.; Kryschi, R., "Die Desinfektion von Wasser in der Brauerei mittels UV–Bestrahlung" [Disinfection of Water in the Brewery by Means of UV Radiation], Journal–Brauwelt, vol. 130, No. 35, pp. 1428–1434, 1990.

Farr, B.M.; Gratz, J.C.; Tartaglion, J.C.; Gretchell–White, S.I.; Groeschell, D.H.M., "Evaluation of Ultraviolet Light for Disinfection of Hospital after Contaminated with Legionella," Journal–Lancet, vol. 2, No. 8612, pp. 669–671, 1988.

Lee, N.E.; Jolley, R.L.; Denton, M.S.; Thompson, J.E., "Ultraviolet Irradiation of Municipal Wastewater: Evaluation of Effects on Organic Constituents," Journal–Environ. Int., vol. 7, No. 6, pp. 403–408, 1982.

Abstract: Ho. K.W.A., "Application of Ultraviolet Disinfection in a Tertiary Wastewater Treatment Plant," Book Monograph, 53 pp., 1982 (NDN–122–0010–8803–7).

Gemne, G.; Hoffner, S.; Stenstroem, T., "Disinfection of Water in a Medical Therapy Pool With Ultraviolet Irradiation," vol. 37, No. 3, pp. 265–274, 1981.

Abstract: Tomowich, D., "UV Disinfection for Wastewater Reuse," Journal–World Water and Environmental Engineering Y World Water Environm. Eng., vol. 21, No. 12, pp. 22–23, 1998 (NDN–057–0008–2462–1), prior art.

Abstract: Jolis, D.; Hirano, R.; Pitt, P., "Teritiary Treatment Using Microfiltration and UV Disinfection for Water Reclamation," vol. 71, No. 2, pp. 224–231, 1999.

Sommer, R.; Haider, T.; Cabaj, A.; Pribil, W.; Lhotsky, M., "Time Dose Reciprocity in UV Disinfection of Water," Journal–Water Science & Technology, vol. 38, No. 12, pp. 145–150, 1998.

Janex, M.L.; Savoye, P.; Do–Quang, Z.; Blatchley, E.R.III; Laine, J.M., "Impact of Water Quality and Reactor Hydrodynamics on Wastewater Disinfection by UV, Use of CFD Modeling for Performance Optimization," Journal–Water Science & Technology, vol. 38, No. 6, pp. 71–78, 1998.

Abstract: Laine, S.; Poujol, T.; Dufay, S.; Baron, J.; Robert, P., "Treatment of Stormwater to Bathing Water Quality by Dissolved Air Flotation, Filtration and Ultraviolet Disinfection," Journal–Water Science & Technology, Vo.. 38, No. 10, pp. 99–105, 1998 (NDN–057–0007–7627–4), prior art.

Gehr, R.; Wright, H., "UV Disinfection of Wastewater Coagulated with Ferric Chloride: Recalcitrance and Fouling Problems," Journal–Water Science & Technology, vol. 38, No. 3, pp. 15–23, 1998.

Eccleston, B., "UV Intensity Levels Affected By Water Quality," Journal–Water Technology, vol. 21, No. 5, pp. 61–68, 1998.

Abstract: Hoyer, O, "Testing Performance and Monitoring of UV Systems for Drinking Water Disinfection," Journal–Water Supply, vol. 16, No. 1–2, pp. 424–429, 1998 (NDN–057–0007–0250–3).

Sommer, R.; Cabaj, A.; Pribil, W.; Haider, T.; Morris, R.; Grabow, W.O.K.; Jofre, J., "Influence of Lamp Intensity and Water Transmittance on the UV Disinfection of Water," Journal–Health–Related Water Microbiology 1996; Water Sci. Technol., vol. 35, No. 11–12, pp. 113–118, 1997.

Rajala–Mustonen, R.L.; Toivola, P.S.; Heinonen–Tanski, H.; Morris, R.; Grabow, W.O.K., "Effects of Peracetic Acid and UV Irradiation on the Inactivation of Coliphages in Wastewater," Journal–Health–Related Water Microbiology 1996; Water Sci. Technol., vol. 35, No. 11–12, pp. 237–241, 1997.

Moreno, B.; Goni, F.; Fernandez, O.; Martinez, J.A.; Astigarraga, M.; Morris, R.; Grabow, W.O.K.; Jofre, J. "The Disinfection of Wastewater by Ultraviolet Light," Journal–Health–Related Water Microbiology 1996; Water Sci. Technol., vol. 35, No. 11–12, pp. 233–235, 1997.

Tree, J.A.; Adams, M.R.; Lees, D.N.; Morris, R.; Grabow, W.O.K.; Jofre, J., "Virus Inactivation During Disinfection of Wastewater by Chlorination and UV Irradiation and the Efficacy of F uper(+) Bacteriophage as a "Viral Indicator"", Journal–Health–Related Water Microbiology 1996; Water Sci. Technol., vol. 35, No. 11–12, pp. 227–232, 1997.

Abstract: Baron, J., "Repair of Wastewater Microorganisms After Ultraviolet Disinfection Under Seminatural Conditions," Journal–Water Environ. Res., vol. 69, No. 5, pp. 992–998, 1997 (NDN–057–0005–2321–9), prior art.

Sommer, R.; Cabaj, A.; Haider, T., "Microbicidal Effect of Reflected UV Radiation in Devices for Water Disinfection," Journal–Water Sci. Technol., vol. 34, No. 7–8, pp. 173–171, 1996.

Abstract: Oppenheimer, J.A.; Jacangelo, J.G.; Laine, J.M.; Hoagland, J.E., "Testing the Equivalency of Ultraviolet Light and Chlorine for Disinfection of Wastewater to Reclamation Standards," Journal–Water Environ. Res., vol. 69, No. 1, pp. 14–24, 1997 (NDN–057–0004–7387–3).

Loge, F.J.; Emerick, R.W.; Heath, M.; Jacangelo, J.; Tchobanoglous, G.; Darby, J.L., "Ultraviolet Disinfection of Secondary Wastewater Effluents: Prediction of Performance and Design", Journal–Water Environ. Res., vol. 68, No. 5, pp. 900–916, 1996.

Abstract: Loge, F.J.; Darby, J.L.; Tchobanoglous, G., "UV Disinfection of Wastewater: Probabilistic Approach to Design", Journal–J. Environ. Eng., vol. 122, No. 12, pp. 1078–1084, 1996 (NDN–057–0004–1702–0).

Perrot, J.Y.; Baron, J., "The Disinfection of Municipal Wastewater by Ultraviolet Light: A French Case Study", Journal–Water Sci. Technol., vol. 32, No. 7, pp. 167–174, 1995.

Gehr, R.; Nicell, J., "Pilot Studies and Assessment of Downstream Effects of UV and Ozone Disinfection of a Physicochemical Wastewater,", Journal–Water Qual. Res. J. Canada, vol. 31, No. 2, pp. 263–281, 1996.

Leveque, F.; Crance, J.M.; Beril, C.; Schwartzbrod, L., "Virucidal Effect of UV Light on Hepatitis A Virus in Sea Water: Evaluation with Cell Culture and RT–PCR," Journal–Water Sci. Technol., vol. 31, No. 5–6, pp. 157–160, 1995.

Abstract: Job, G.D.; Trengove, R.; Realey, G.J., "Trials Using a Mobile Ultraviolet Disinfection System in South West Water," Journal–J. Inst. Water Environ. Manage., vol. 9, No. 3, pp. 257–263, 1995 (NDN–057–0003–2747–9).

Rodriquez, J.; Gagnon, S., "UV Provides Rx for Medical Water," Journal–Water Technol, vol. 19, No. 4, pp. 34–42, 1996.

Blatchley, E.R. III; Bastian, K.C.; Duggirala, R.K.; Alleman, J.E.; Moore, M.; Schuerch, P., "Ultraviolet Irradiation and Chlorination/Dechlorination for Municipal Wastewater Disinfection: Assessment of Performance Limitations," Journal–Water Environ. Res., vol. 68, No. 2, pp. 194–204, 1996.

Cairns, W.L., "UV Technology for Water Supply Treatment," Journal–Water Supply, vol. 13, No. 3–4, pp. 211–214, 1995.

Liu, Z.; Stout, J.E.; Tedesco, L.; Boldin, M.; Hwang, C.; Yu, V.L., "Efficacy of Ultraviolet Light in Preventing Legionella Colonization of a Hospital Water Distribution System," Journal–Water Res., vol. 29, No. 10, pp. 2275–2280, 1995.

Abstract: Boisdon, V., "Water Disinfection Efficiency by Chemical Processes and UV Radiation," Journal–Tech. Sci. Methods, Genie–Urbain–Genie Rural, No. 3, pp. 228–236, 1995 (NDN–057–0002–4401–0).

Carnimeo, D.; Contini, E.; DiMarino, R.; Donadio, F.; Liberti, L.; Ranieri, E., "Wastewater Disinfection by UV at Trani Municipal Plant," Journal–Water Sci. Technol., vol. 30, No. 4, pp. 125–132, 1994.

Moore, N.J.; Margolin, A.B., "Efficacy of Nucleic Acid Probes for Detection of Poliovirus in Water Disinfected by Chlorine, Chlorine Dioxide, Ozone, and UV Radiation," Journal–Appl. Environ. Microbiol., vol. 60, No. 11, pp. 4189–4191, 1994.

De Pue, S.E.; Dudley, R.E., "Water Treatment on the Move, Ultraviolet Disinfecting Works Almost Anywhere," Journal–Water Technol., vol. 17, No. 10, pp. 80–83, 1994.

Abu–Ghararah, Z.H., "Effect of Temperature on the Kinetics of Wastewater Disinfection Using Ultraviolet Radiation," Journal–J. Environ. Sci. Health, Part A, vol. A29, No. 3, pp. 585–603, 1994.

Lund, V.; Hongve, D., "Ultraviolet Irradiated Water Containing Humic Substances Inhibits Bacterial Metabolism," Journal–Water Res., vol. 28, No. 5, pp. 1111–1116, 1994.

Lindenauer, K.G.; Darby, J.L., "Ultraviolet Disinfection of Wastewater: Effect of Dose on Subsequent Photoreactivation," Journal–Water Res., vol. 28, No. 4, pp. 805–817, 1994.

Darby, J.L.; Snider, K.E.; Tchobanoglous, G., "Ultraviolet Disinfection for Wastewater Reclamation and Reuse Subject to Restrictive Standards," Journal–Water Environ. Res., vol. 65, No. 2, pp. 169–180, 1993.

LeChevallier, M.W.; Norton, W.D.; Lee, R. G., "Occurrence of Giardia and Cryptosporidium spp. In Surface Water Supplies" Journal–Applied and Environmental Microbiology, Sep. 1991, vol. 57, No. 9, pp. 2610–2616.

Tyzzer, E.E., "A Sporozoan Found in the Peptic Glands of the Common Mouse," Article from the Laborary of the Caroline Brewer Croft Fund Cancer Commission of Harvard University, prior art.

Rose, J.B., Occurrence and Significance of Cryptosporidium in Water, Journal AWWA, Research & Technology, Feb. 1988, pp. 53–58.

Rose, J.B., "Survey of Potable Water Supplies for Cryptosporidium and Giardia," Journal–Environ. Sci. Technol., vol. 25, No. 8, 1991, pp. 1383–1400.

Nime, F.A.; Burek, J.D.; Page, D.L.; Holscher, M.A.; Yardley, J.H., "Acute Enterocolitis in a Human Being Infected with the Protozoan Cryptosporidium," Journal–Gastroenterology, vol. 70, No. 4, pp. 592–598, 1976.

LeChevallier, M.W.; Norton, W. D., "Giardia and Ctyptosporidium in Raw and Finished Water" Journal AWWA, Sep. 1995, pp. 5465.

David R. Lide, Ph.D., CRC Handbook of Chemistry and Physics, $73^{rd}$ Edition, 1992–1993.

Dertiende, Herziene Uitgave, Door Prof. Dr. Guido Geerts En Drs. Ton Den Boon, Van Dale Groot Woordenboek Der Nederlandse Taal, j–r, 1999.

DVGW Regelwerk, Technische Mitteilung Merkblatt, W 293, UV–Anlagen zur Desinfektion von Trinkwasser, Oct. 1994.

Holleman–Wiberg, Lehrbuch der Anorganischen Chemie, 91–100, verbesserte und stark erweirerte Auflage von, Nils Wiberg, WDEG, New York 1985.

Excerpts from "Disinfection, Sterilization and Preservation (1991)".

Gadgil et al., "Field testing UV Disinfection of drinking Water," Paper presented at the $23^{rd}$ WEDC Conference "Water Sanitation for All" Sep. 1–5, 1997, Proceedings Published 1997 by the Water Engineering Development Centre, University of Loughborough, UK.

Wolfe, "Ultraviolet disinfection of potable water," Environmental Science and Technology, Vo. 24, pp. 768–772 (1990).

Carlson et al, "Project Summary: Ultraviolet Disinfection of Water for Small water Supplies," Office of Research and Development, US Environmental Protection Agency, Cincinnati, OH 1985, EPA/500/52–85/092, prior art.

"Ultraviolet Light Disinfection Technology in Drinking Water Application—An Overview,", US Environmental Protection Agency, Sep. 1996, EPA 811–R–96–002.

"Evaluation of the Safe Water Solutions LLC Cryptosporidium Inactivation Device for Inactivation of Cryptosporidium Parvum Oocysts," Mar. 1996.

Clancy et al, "Ultraviolet Irradiation (UV) for the Inactivation of Cryptosporidium in Water," paper presented at the 1997 AWWA Water Quality Technology Conference (document missing).

* cited by examiner

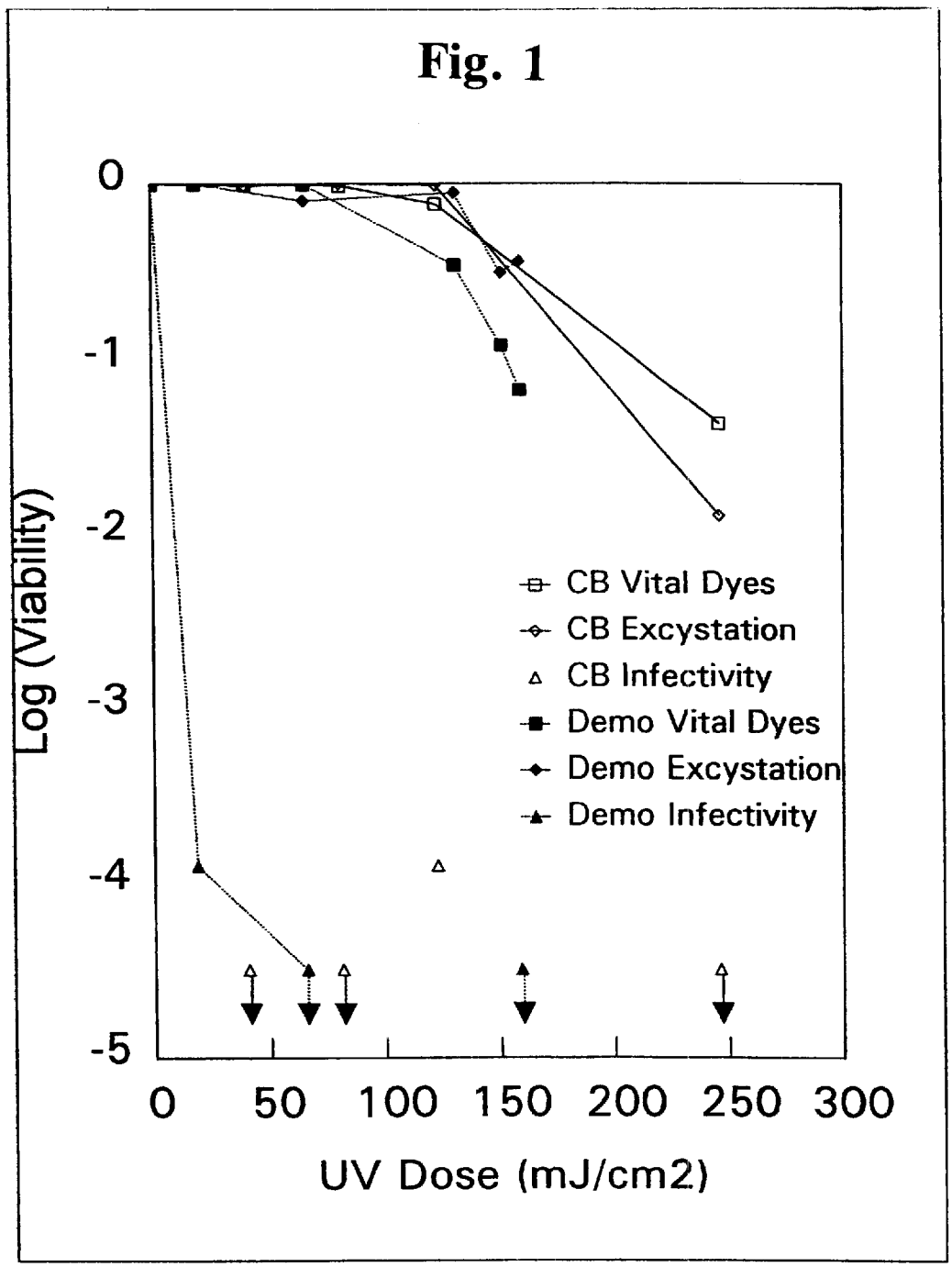

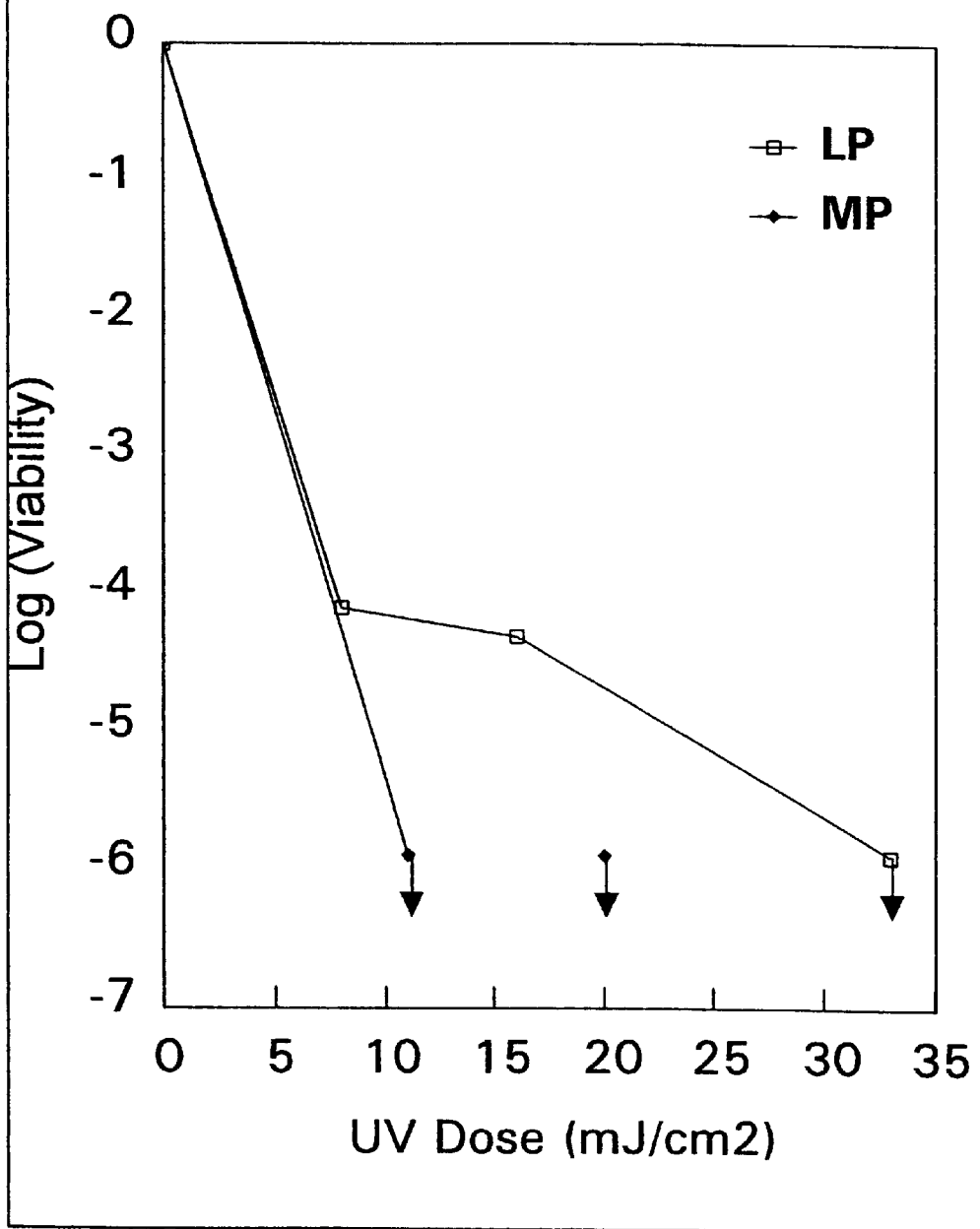

METHOD FOR THE INACTIVATION OF CRYPTOSPORIDIUM PARVUM USING ULTRAVIOLET LIGHT

CROSS-REFERENCE

The present application is a continuation-in-part application of Ser. No. 09/078,116, filed May 13, 1998, entitled METHOD FOR PREVENTING REPLICATION IN CRYPTOSPORIDIUM PARVUM USING ULTRAVIOLET LIGHT, now U.S. Pat. No. 6,129,893.

FIELD OF THE INVENTION

The present invention relates to a method for inactivating *Cryptosporidium parvum* in water and in particular to a method for the prevention of *Cryptosporidium parvum* and other protozoans, such as *Giardia muris,* from establishing infection in human hosts, as measured by the ability to infect neo-natal mice, using low doses of ultraviolet light.

BACKGROUND OF THE INVENTION

It has been generally well recognized that it is necessary to kill or inactivate protozoan oocysts so that they cannot infect susceptible hosts. This is especially important in drinking water. One such method is the use of ultraviolet ("UV") light. The prior art teaches that a UV dose of at least 3000 $mJ/cm^2$ is required to inactivate *Cryptosporidium parvum* (Lorenzo-Lorenzo et al., J. Parasitol. 1993, 79, 67–70) and *Giardia muris* (E. L. Jarol, "Effect of Disinfectants on Giardia Cysts", CRC Critical Reviews in Environmental Control, 1988, 18, 1–28). Snowball and coworkers (UK Patent Application #9416287.2, Nov. 8, 1984; Wat. Res., 1995, 29, 2583–2586) developed an apparatus that first filtered out Cryptosporidium oocysts and then exposed them to UV doses of 700–800 $mJ/cm^2$. The patent teaches the use of 2 $\mu m$ screen filters to trap Cryptosporidium oocysts which are then irradiated with a bank of low-pressure Hg lamps for a UV dose of 350–400 $mJ/cm^2$. The filter is then backwashed onto a second filter and the irradiation is repeated for a total dose of 700–800 $mJ/cm^2$. The patent discloses that the treatment "kills" the organisms.

M. J. Lorenzo-Lorenzo, M. E. Area-Mazea, I. Villacorta-Martinez de Maturana and D. Duran-Oreiro ["Effect of Ultraviolet Disinfection of Drinking Water on the Viability of *Cryptosporidium parvum* Oocysts", *J. Parasitol.* 1993, 79(1), 67–70] report the prevention of infection in mice after exposure to at least 150 min. of UV from a (presumably) low-pressure Hg lamp. Although the paper is not clear, it can be inferred that the UV dose applied was over 5000 $mJ/cm^2$ to obtain better than 2 logs reduction in infectivity. The authors claim that exposure to UV for 150 min. or more "eliminates" infectivity, but they give no mechanism other than to say "UV radiation disrupts DNA by causing formation of thy[ia]mine dimers, and high levels may lead to cell death". At the UV doses they applied, the effects observed almost certainly arose from cell death.

In a paper by A. Bushnell, W. Clark, J. Dunn and K. Salisbury ["Pulsed Light Sterilization of Products Packaged by Blow-Fill-Seal Techniques", *Pharm. Engin.* 1997, September/October, 74–83], a pulsed UV technique for "sterilizing" surfaces containing bacteria, fungi, spores, viruses, protozoa and oocysts is described. The required UV doses were reported to be over 1000 $mJ/cm^2$. The effectiveness of the method was assayed using mouse infectivity. At the reported UV doses, the effects were believed to be due to cell death.

In a paper by R. LaFrenz ["High Intensity Pulsed UV for Drinking Water Treatment", *Proc. AWWA WQTC Conference,* Denver, Colo., November, 1997], a similar pulsed system was described. While very few details were given, it appears that mouse infectivity assay was used and 6 logs of "inactivation" of Cryptosporidium was obtained at energy levels of approximately 200 $mJ/cm^2$ and greater. The paper claims that the pulsed UV overcomes the "DNA repair mechanism"; however, the UV doses applied are much larger than required with either a steady-state medium pressure or low pressure Hg lamp, as shown herein.

From the references cited above, we infer that the prior art teaches that very large UV doses (>200 $mJ/cm^2$ and up to 5000 $mJ/cm^2$) are required to inactivate Cryptosporidium by "killing" the organisms. Accordingly, it is an object of the invention to provide a method using ultraviolet light to treat water in an effective way so that Cryptosporidium oocysts cannot infect susceptible hosts or, in other words, to "disinfect" the water in regard to Cryptosporidium oocysts that may be present. It is another object of the invention to provide a method using ultraviolet light from a medium-pressure mercury lamp to render the Cryptosporidium oocysts unable to infect. It is yet another object of the present invention to provide a method using ultraviolet light that is cost-effective in treating drinking water to eliminate the potential for infection by Cryptosporidium oocysts and Giardia cysts. The final object of the invention is to provide a method using ultraviolet light from a low-pressure mercury lamp to render Cryptosporidium oocysts and Giardia cysts unable to infect.

SUMMARY OF THE INVENTION

Generally it has been discovered that it is not necessary to "kill" pathogens, such as *Cryptosporidium parvum* or *Giardia muris* with ultraviolet light in order to prevent infection; one need only apply enough ultraviolet light to prevent the organism from "replicating". The method of the present invention prevents replication (cell mitosis) by inactivating the DNA to prevent infection. The UV doses required to prevent replication are orders of magnitude lower than required to "kill" the oocysts. This means that the cost of UV treatment to prevent infection by Cryptosporidium oocysts will be markedly lower.

It has been found that when biological organisms are exposed to ultraviolet light (UV) in the range of 200–300 nm, the UV can be absorbed by DNA, RNA, and proteins. Absorption by proteins can lead to rupture of cell walls and death of the organism. Absorption by DNA or RNA (specifically by thymine bases) is known to cause inactivation of the DNA or RNA double helix strands through the formation of thymine dimers. If enough of these dimers are created in DNA, the DNA replication process is disrupted and hence, in mitosis, the cell cannot replicate. Cells that cannot replicate cannot infect. The present invention utilizes UV doses substantially lower (to achieve the state of hindered replication) by orders of magnitude than those required to cause oocyst death.

The present invention preferably utilizes a broad band (200–300 nm) medium-pressure mercury UV lamp to achieve the disinfection. In another embodiment of the invention, a low-pressure mercury (essentially monochromatic) UV lamp can be used. The dose required with a medium-pressure lamp was measured to be 11 mJ/cm$^2$ to achieve better than 5.9 log disinfection. From this it can be inferred that a dose of 7 mJ/cm$^2$ will achieve better than 4 log disinfection (99.99%) and 3.6 mJ/cm$^2$ will achieve better than 2 log disinfection (99%). For low pressure lamps a dose of 8 and 16 mJ/cm$^2$ was required to achieve 4.1 and 4.3 log disinfection, respectively. Thus, the dose levels of UV are significantly lower than those used before resulting in significantly lower power levels needed to achieve the results. It has been found that inactivation of Cryptosporidium and similar organisms such as Giardia occurs at dosages from about 1 mJ/cm$^2$. Accordingly, the method provides a substantial improvement in the cost effectiveness of UV for the disinfection of contaminated drinking water as regards to Cryptosporidium oocysts and Giardia cysts that may be present. Other advantages will become apparent from a perusal of the following detailed description of a presently preferred embodiment of the invention.

BRIEF DESCRIPTION OF THE DRAWINGS

FIG. 1 is a chart that shows the correlation between bench-scale and demonstration-scale tests and the difference between "in vitro" and "in vivo" methods.

FIG. 2 is a chart that shows the correlation between tests using low-pressure versus medium-pressure mercury are UV lamps.

PRESENTLY PREFERRED EMBODIMENT

Experiments were conducted on two different sets of apparatus: a bench-scale collimated beam setup and a demonstration-scale UV reactor.

A well-known bench-scale collimated beam apparatus was used in the test. An upper lamp housing can contain either a 15 W low-pressure Hg lamp (monochromatic at 254 nm) or a 1 kW Rayox medium-pressure Hg lamp (emitting over a broad range from 200–300 nm). Each lamp has its own power supply in the lower housing. A black plastic collimator (48 cm long and 6.4 cm diameter) extends vertically down from the lamp housing with a pneumatically-driven shutter in between. The cell suspension (in finished water from the Mannheim Water Treatment Plant, Kitchener, Ontario, Canada) to be irradiated is placed in a Petri dish (with a stir bar) on top of a stirring motor below the collimator and exposed for a fixed length of time to achieve the desired UV dose. The UV irradiance is measured with an Interational Light Model 1400 Radiometer with a Model SED240 detector. Proper account is taken of the variation of the detector sensitivity with wavelength, the attenuation of irradiance in the water and of the irradiance distribution over the top of the Petri dish. The UV dose (mJ/cm$^2$) is the average UV irradiance (mW/cm$^2$) in the water times the exposure time (s).

Demonstration-scale challenges of *Cryptosporidium parvum* and *Giardia muris* were carried out on filtered water at the Mannheim Water Treatment Plant in Kitchener, Ontario, Canada with a 111 L (29.4 gal) UV reactor containing 6×1 kW Rayox Sentinel™ medium-pressure UV lamps mounted horizontally across a tower type UV reactor. The organisms were introduced upstream of a static mixer ahead of the reactor and collected on 1 micron filters after the reactor. The overall flow rate during each test was about 215 gpm (814 L/min). The filters were shipped to St. Albans, Vt. where the organisms were extracted from the filters and concentrated. All organisms were subjected to in vitro assays (fluorogenic vital dyes and excystation); four of the Cryptosporidium samples were shipped to the Department/Laboratory of the University of Arizona for mouse infectivity assays.

The UV-treated oocysts were enumerated with a hemocytometer, using bright-field microscopy to determine the concentration of oocysts present in each tube. These preliminary counts were used to calculate the dilutions that were necessary for preparation of oocyst inocula for neonatal mice.

Upon arrival of the oocysts at the University of Arizona, the infectivity of the oocysts was determined by their inoculation into 4 to 6-day-old CD-1 outbred mice. The mice were challenged with oocyst inocula prepared in sterile water adjusted to pH 7. All inocula were prepared by serial dilution from a pre-enumerated oocyst suspension. A calibrated pipette was used for all dilutions and following dilution, oocysts inocula were re-enumerated before they were fed to the mice. The counts were performed and cross-checked by two technicians. The oocysts were administered orally in 10 $\mu$L inocula with a dedicated, calibrated pipette equipped with a standard tip. The inocula were administered slowly with the mouse held gently in the palm of the technician's hand until the entire inoculum was swallowed. The animals were sacrificed seven days post-inoculation and approximately 2 cm of terminal ileum was excised. The tissue samples were fixed in formalin, embedded in paraffin, sectioned, mounted on microscope slides, stained, and examined for the presence of endogenous stages of *C. parvum* in the brush-borders of the intestinal villi. Specimens with parasites were scored positive and those without parasites were scored negative.

The UV dose (mJ/cm$^2$) applied in the reactor was calculated from the average irradiance (mW/cm$^2$) (determined from a sophisticated point source summation model of the reactor) times the residence time in the reactor (about 8.3 s). The UV dose was varied by turning one or two lamps on at "low" or "full" power.

A subsequent set of bench-scale experiments was conducted to assess differences between low-and medium-pressure Hg lamps. The conditions for these experiments were essentially the same as that for the bench-scale experiments described above except that one set of experiments was conducted using the low-pressure Hg lamp and one set with the medium-pressure Hg lamp.

SUMMARY OF THE RESULTS

Assays

Two in vitro assays (fluorogenic vital dyes and maximized excystation) and one in vivo assay (neonatal mouse infectivity) were used to assess the viability and infectivity of the *Cryptosporidium parvum* oocysts for both the bench-and demonstration-scale experiments. In addition, one in vitro assay (maximized excystation) was performed in the demonstration scale experiments for *Giardia muris* cysts. Also in vivo testing for Giardia was performed.

Bench-Scale Study

Viability and Infectivity of Untreated and Process Control Oocysts of Cryptosporidium The initial viability assessment in the trip control (untreated oocyst suspensions) indicated high viability with the fluorogenic vital dyes (91%±2%) and maximized in vitro excystation (76%±4%. These results were corroborated with mouse infectivity, which indicated that 75 oocysts were necessary for 56% infection in CD-1 neonatal mice. In the process control (oocysts subjected to all experimental procedures without exposure to UV light), the fluorogenic vital dyes indicated a viability of 85±3% and maximized in vitro excystation a viability of 86%. For the process controls, an inoculum of 50 oocysts caused approximately 80% infection in neonatal mice. These data were used to "normalize" the experimental viabilities for the in vitro assays by multiplying by (1/0.85=1.18) in the case of fluorogenic vital dyes and by (1/0.86=1.16) in the case of maximized excystation.

Viability and Infectivity of UV-exposed Oocysts

Four UV doses were examined to assess their effect on oocyst viability and infectivity. The normalized in vitro viability data for the UV-exposed oocysts are given in Table 1a. The log viability factor is the logarithm of the ratio of the viability percentage relative to that of the process control.

The in vivo neonatal mouse infectivity data are given in Table 1b and were ascertained from microscopic examination of tissue sections derived from the ileum of individual mice, seven days past infection. The percentage infectivity for a given dose was determined from the ratio of infected mice to the total number of mice receiving that dose. In order to establish a log viability for infection, the percentage infectivity values were extrapolated from a log it dose response model, which was generated from previous infectivity studies and has the following equation.

$$\text{response log it}=-7.536+3.867\log_{10}\text{Dose}=\ln[P/(1-P)]$$

where P is the proportion of mice infected. The response log it is very similar to that described by Finch et al. [Finch, G. R., Daniels, C. W., Black, E. K., Schaefer III, F. W. and Belosovic, M. 1993. "Dose Response of *Cryptosporidium parvum* in Outbred Neonatal CD-1 Mice". Applied and Environmental Microbiology. 59(11):3661–3665.] and is used to determine the number of infectious oocysts in a given oocyst inoculum.

For example, oocyst exposure to 123 $mJ/cm^2$ of medium-pressure UV caused infection in 1 of 25 mice at an inoculum of $1.0\times10^5$ oocysts. Substitution of these data into the log it response equation indicates $$\text{Response log it}=\ln[0.04/0.96]=-3.178$$

Substituting:

$$-3.178=-7.536+3.867\log_{10}\text{Dose}$$

$$\log_{10}(\text{no. of infectious oocysts})=(7.536-3.178)/3.867=1.127$$

No. of infectious oocysts=13

This calculation indicates that following treatment of oocysts with UV and administration of an inoculum of $1.0\times10^5$ oocysts, approximately 13 oocysts were capable of causing infection in mice.

The log viability for infection was calculated by the following equation:

$$\text{log viability (for infection)}=\log_{10}[(\text{no. of infectious oocysts})/(\text{original inoculum})]$$

In the example, $$\text{log viability (for infection)}=\log_{10}[13/100{,}000]=-3.9$$

These infectivity data in Table 1b indicate that the in vitro assays greatly underestimate oocyst inactivation when compared to in vivo mouse infectivity.

TABLE 1a

Normalized Viability Factors (percent) for in vitro Bench-Scale Tests

| UV Dose ($mJ/cm^2$) | Viability Percentage* | | Log Viability | |
|---|---|---|---|---|
| | Vital Dyes | Excystation | Vital Dyes | Excystation |
| 41 | 100 | 98 | 0.00 | −0.01 |
| 82 | 98 | 99 | −0.01 | 0.00 |
| 123 | 78 | 98 | −0.11 | −0.01 |
| 246 | 4.4 | 1.3 | −1.36 | −1.89 |

*Values over 100% are considered to be 100%

TABLE 1b

Percentage Neo-natal Mouse Infectivity for in vitro Bench-Scale Tests

| UV Dose ($mJ/cm^2$) | Percentage infectivity and Inoculum (bold numbers) | | | Log Viability |
|---|---|---|---|---|
| | Inoculum 1 | Inoculum 2 | Inoculum 3 | |
| 0 (Trip Control) | 35% (8/23) | 56% (14/25) | 79% (19/24) | |
| | 25 | 75 | 150 | |
| 0 (Process | 82% (22/27) | 100% (24/24) | 100% (27/27) | |
| Control) | 50 | 500 | 5000 | 0.00 |
| 41 | 0% (0/28) | 0% (0/26) | 0% (0/24) | |
| | 1,000 | 10,000 | 100,000 | <−4.5 |

TABLE 1b-continued Percentage Neo-natal Mouse Infectivity for in vitro Bench-Scale Tests Percentage infectivity and Inoculum (bold numbers)

| UV Dose (mJ/cm$^2$) | Inoculum 1 | Inoculum 2 | Inoculum 3 | Log Viability |
|---|---|---|---|---|
| 82 | 0% (0/27) | 0% (0/26) | 0% (0/24) | |
|  | 1,000 | 10,000 | 100,000 | <−4.5 |
| 123 | 0% (0/25) | 0% (0/23) | 4% (1/25) | |
|  | 1,000 | 10,000 | 100,000 | −3.9 |
| 246 | 0% (0/24) | 0% (0/27) | 0% (0/27) | |
|  | 1,000 | 10,000 | 100,000 | <−4.5 |

Demonstration Scale Study
Viability and Infectivity of Untreated and Process Control Cryptosporidium Oocysts and Giardia Cysts The initial viability assessment in the trip control (untreated Cryptosporidium oocyst suspensions) indicated high viability with the fluorogenic vital dyes (82%±4%) and maximized in vitro excystation (81%±8%). These results were corroborated with mouse infectivity, which indicated that 75 oocysts were necessary for 35% infection in CD-1 neonatal mice. In two process controls (oocysts subjected to all experimental procedures without exposure to UV light), the fluorogenic vital dyes indicated an average viability of 77±5%, while maximized in vitro excystation indicated an average viability of 38%±8% for Cryptosporidium and 53%±23% for Giardia. For the process controls, an inoculum of 50 oocysts caused approximately 44% infection in neonatal mice. These data were used to "normalize" the experimental viabilities for the in vitro assays by multiplying by (1/0.72=1.39) in the case of fluorogenic vital dyes and by (1/0.38=2.63) in the case of maximized excystation for Cryptosporidium oocysts and (1/0.53=1.89) for Giardia.

Viability and Infectivity of UV-exposed Oocysts

In the demonstration-scale disinfection experiments, five UV doses were examined to assess their effects on *Cryptosporidium parvum* viability with three doses used to asses infectivity. Only in vitro excystation was used to assess the viability of *Giardia muris* cysts.

The normalized in vitro viability data for the UV-exposed oocysts and cysts are given in Table 2a and the in vivo neonatal mouse infectivity data are given in Table 2b. These data again indicate that the in vitro assays greatly underestimate oocyst inactivation when compared to in vivo mouse infectivity.

TABLE 2a

Normalized Viability Factors (percent) for in vitro Demonstration-Scale Tests

| | Viability Percentage* | | | Log Viability | | |
|---|---|---|---|---|---|---|
| | Cryptosporidium | | Giardia | Cryptosporidium | | Giardia |
| UV Dose (mJ/cm$^2$) | Vital Dyes | Excy-station | Excy-station | Vital Dyes | Excy-station | Excy-station |
| 19 | 100 | 100 | 100 | 0.00 | 0.00 | 0.00 |
| 66 | 100 | 82 | 100 | 0.00 | −0.09 | 0.00 |
| 131 | 35 | 90 | 69 | −0.46 | −0.05 | −0.16 |
| 151 | 12 | 32 | 43 | −0.92 | −0.50 | −0.37 |
| 159 | 6.8 | 36 | 38 | −1.17 | −0.44 | −0.42 |

*Values over 100% are considered to be 100%

TABLE 2b

Percentage Neo-natal Mouse Infectivity for in vitro Demonstration-Scale Tests for Cryptosporidium Percentage infectivity and Inoculum (bold numbers)

| UV Dose (mJ/cm$^2$) | Inoculum 1 | Inoculum 2 | Inoculum 3 | Log Viability |
|---|---|---|---|---|
| 0 (Trip Control) | 5% (2/38) | 35% (14/40) | 65% (15/23) | |
|  | 25 | 75 | 150 | |
| 0 (Process Control) | 44% (11/25) | 100% (20/20) | 100% (23/23) | |
|  | 50 | 500 | 5000 | 0.00 |
| 19 | 0% (0/18) | 0% (0/18) | 4.5% (1/22) | |
|  | 1,000 | 10,000 | 100,000 | −3.9 |
| 66 | 0% (0/22) | 0% (0/26) | 0% (0/25) | |
|  | 1,000 | 10,000 | 100,000 | <−4.5 |

TABLE 2b-continued

Percentage Neo-natal Mouse Infectivity for in vitro
Demonstration-Scale Tests for Cryptosporidium Percentage infectivity
and Inoculum (bold numbers)

| UV Dose (mJ/cm$^2$) | Inoculum 1 | Inoculum 2 | Inoculum 3 | Log Viability |
|---|---|---|---|---|
| 159 | 0% (0/24) 1,000 | 0% (042) 10,000 | 0% (0/24) 100,000 | <−4.5 |

Comparison of Bench-and Demonstration-Scale Disinfection Studies to Assess Oocyst Inactivation The oocyst inactivation data are illustrated in FIG. 1 as log(viability ratio versus UV). The viability ratio is defined as the ratio of the viability of the UV-treated oocysts to that of the process control versus UV dose. The dramatic difference between the in vitro (fluorogenic vital dyes and excystation) and in vivo (neonatal mouse infectivity) assays may be explained in the context that the in vitro assays measure integrity/permeability of the oocyst wall, not the ability of the oocyst to infect its host; whereas the in vivo assay measures the ability of the oocysts to infect a susceptible host.

Validation of the UV Dose for the Demonstration-scale Study

The UV dose for the demonstration-scale study depends on the average irradiance calculated from a complex mathematical model. It is thus important to have an independent assessment of the accuracy of the calculation. An examination of FIG. 1 shows an excellent agreement between the bench-scale and demonstration-scale studies especially considering the uncertainties associated with these assays. Thus the UV dose calculated in the demonstration-scale studies can be considered validated by the excellent agreement with the experimentally obtained data from the collimated beam tests.

Bench-Scale Study Comparing Effects of Low- and Medium-Pressure Hg Lamps

The effects of three low-pressure UV doses (8, 16 and 33 mJ/cm$^2$) and two medium-pressure UV doses (11 and 20 mJ/cm$^2$) on the viability and infectivity of *Cryptosporidium parvum* oocysts (suspended in Mannheim finished water) were examined.

Viability and Infectivity of Untreated and Process Control Oocysts of Cryptosporidium The initial viability assessment in untreated oocyst suspensions indicated a viability of 80%±4% with the fluorogenic vital dyes and 71%±6% by maximized in vitro excystation. In the process control (oocysts subjected to all experimental procedures without exposure to UV light), the fluorogenic vital dyes indicated a viability of 68±4% and maximized in vitro excystation a viability of 67%. For the process controls, an inoculum of 50 oocysts caused approximately 53% infection in neonatal mice. These data were used to "normalize" the experimental viabilities for the in vitro assays by multiplying by (1/0.68=1.47) in the case of fluorogenic vital dyes and by (1/0.67=1.49) in the case of maximized excystation.

Viability and Infectivity of UV-exposed Oocysts

The normalized in vitro viability data for the UV-exposed oocysts are given in Table 3a and the in vivo neonatal mouse infectivity data are given in Table 3b. These data again indicate that the in vitro assays greatly underestimate oocyst inactivation when compared to in vivo mouse infectivity. Also, there is a definite difference between the data for the low-pressure Hg lamp and that for the medium-pressure Hg lamp. None of the mice became infected in any of the medium-pressure experiments, whereas there were definite indications of infectivity for at least the two lowest low-pressure UV doses. To achieve 5.9 logs inactivation, it is preferable to administer at least between 11 and 22 mJ/cm$^2$ with a low-pressure Hg lamp. Typically, 11 mJ/cm$^2$ suffices for the medium-pressure Hg lamp. However, it has been found that there is little difference in UV sensitivity between the medium-pressure and low-pressure Hg lamps.

TABLE 3a

Normalized Viability Factors (percent) for in vitro
Bench-Scale Tests Comparing Low-Pressure (LP)
versus Medium-Pressure (MP) Hg Lamps

| UV Dose | Viability Percentage* | | Log Viability | |
|---|---|---|---|---|
| (mJ/cm$^2$) | Vital Dyes | Excystation | Vital Dyes | Excystation |
| LP-8 | 94 | 78 | −0.03 | −0.11 |
| LP-16 | 100 | 88 | 0.00 | −0.06 |
| LP-33 | 91 | 91 | −0.04 | −0.04 |
| MP-11 | 100 | 61 | 0.00 | −0.22 |
| MP-20 | 100 | 72 | 0.00 | −0.14 |

*Values over 100% are considered to be 100%

TABLE 3b

Percentage Neo-natal Mouse Infectivity for in vitro Bench-Scale Tests
Comparing Low-Pressure (LP) versus Medium-Pressure (MP) Hg Lamps Percentage infectivity and Inoculum (bold numbers)

| UV Dose (mJ/cm$^2$) | Inoculum 1 | Inoculum 2 | Inoculum 3 | Log Viability |
|---|---|---|---|---|
| 0 (Process Control) | 53% (10/19) 50 | 79% (19/24) 100 | 100% (6/6) 1000 | 0.00 |

TABLE 3b-continued

Percentage Neo-natal Mouse Infectivity for in vitro Bench-Scale Tests
Comparing Low-Pressure (LP) versus Medium-Pressure (MP) Hg Lamps

| UV Dose (mJ/cm$^2$) | Percentage infectivity and Inoculum (bold numbers) | | | Log Viability |
| --- | --- | --- | --- | --- |
| | Inoculum 1 | Inoculum 2 | Inoculum 3 | |
| LP-8 | 0% (0/17)<br>10$^4$ | 5% (1/19)<br>10$^5$ | 42% (8/19)<br>10$^6$ | −4.1 |
| LP-16 | 0% (0/27)<br>10$^4$ | 0% (0/20)<br>10$^5$ | 26% (5/19)<br>10$^6$ | −4.3 |
| LP-33 | 0% (0/21)<br>10$^4$ | 4% (1/23)<br>10$^5$ | 0% (0/24)<br>10$^6$ | <−5.9 |
| MP-11 | 0% (0/20)<br>10$^4$ | 0% (0/25)<br>10$^5$ | 0% (0/19)<br>10$^6$ | <−5.9 |
| MP-20 | 0% (0/23)<br>10$^4$ | 0% (0/22)<br>10$^5$ | 0% (0/24)<br>10$^6$ | <−5.9 |

TABLE 4

Preliminary Results of the Dosage Relationship
of Cryptosporidium and Gardia.

| UV Dose (mJ/cm$^2$) | Cryptosporidium | Giardia |
| --- | --- | --- |
| 0 | 0 | |
| 3.4 | 2.0 | |
| 4.8 | 2.0 | |
| 8 | 3.5 | |
| 16 | 3.0 | |
| 34 | 3.5 | |
| 0 | | 0 |
| 5 | | 2.3 |
| 10 | | 2.6 |
| 21 | | 2.9 |
| 83 | | 2.8 |

While presently referenced embodiments of the invention have been described, the invention may be otherwise embodied within the scope of the appended claims.

What is claimed:

1. A method for the prevention of infection from cryptosporidium oocysts found in drinking water comprising irradiating said water with continuous ultraviolet light having predominant wavelength bands that falls within about 200 nanometers to about 300 nanometers with a dose of from about 1 mJ/cm$^2$ to about 175 mJ/cm$^2$.

2. A method as set forth in claim 1 wherein said dose is from about 3.5 mJ/cm$^2$ to about 175 mJ/cm$^2$.

3. A method as set forth in claim 1 or 2 wherein said ultraviolet light substantially comprises a wavelength of about 254 nanometers.

4. A method as set forth in claim 1 or 2 wherein said ultraviolet light is produced by one of a low pressure mercury lamp or a medium pressure mercury lamp.

5. A method as set forth in claim 4 wherein said ultraviolet light is produced by a low pressure mercury lamp.

6. A method as set forth in claim 4 wherein said ultraviolet light is produced by a medium pressure mercury lamp.

7. A method for the prevention of replication of cryptosporidium oocysts or giardia cysts in drinking water treatment comprising irradiating said water with a continuous source of light having predominant wavelength bands that falls within about 200 nm to about 300 nm and a dose of from about 1 mJ/cm$^2$ to about 175 mJ/cm$^2$.

8. A method as set forth in claim 7 wherein said dose is from about 3.5 mJ/cm$^2$ to about 175 mJ/cm$^2$.

9. A method as set forth in claim 7 or 8 wherein said light substantially comprises a wavelength of about 254 nanometers.

10. A method as set forth in claim 7 or 8 wherein said light is produced by one of a low pressure lamp or a medium pressure lamp.

11. A method as set forth in claim 10 wherein said light is produced by a low pressure lamp.

12. A method as set forth in claim 10 wherein said light is produced by a medium pressure lamp.

13. A method of treating drinking water containing contaminants including cryptosporidium comprising exposing said water to a continuous broad band of ultraviolet radiation with a dose of about 1.0 mJ/cm$^2$ to about 175 mJ/cm$^2$, wherein said exposing step is the sole process for rendering cryptosporidium in said drinking water noninfectious.

14. A method as set forth in claim 13 wherein said dose is from about 3.5 mJ/cm$^2$ to about 175 mJ/cm$^2$.

* * * * *